(12) United States Patent  (10) Patent No.: US 7,656,997 B1
Anjelly  (45) Date of Patent: Feb. 2, 2010

(54) METHOD AND APPARATUS FOR AUTOMATED, DIGITAL, RADIOGRAPHIC INSPECTION OF PIPING

(75) Inventor: Samir Anjelly, Islip, NY (US)

(73) Assignee: VJ Technologies, Bohemia, NY (US)

( * ) Notice: Subject to any disclaimer, the term of this patent is extended or adjusted under 35 U.S.C. 154(b) by 0 days.

(21) Appl. No.: 12/283,845

(22) Filed: Sep. 15, 2008

(51) Int. Cl.
*G01N 23/02* (2006.01)
(52) U.S. Cl. ....................................... 378/59
(58) Field of Classification Search ............... 378/4–20, 378/57–60, 62
See application file for complete search history.

(56) References Cited

U.S. PATENT DOCUMENTS

| | | | | |
|---|---|---|---|---|
| 5,698,854 A | 12/1997 | Gupta | ..................... | 250/358.1 |
| 5,864,601 A | 1/1999 | Cattorini | ..................... | 378/59 |
| 6,925,145 B2 | 8/2005 | Batzinger | ..................... | 378/59 |
| 7,319,738 B2 | 1/2008 | Lasiuk | ........................ | 378/59 |

*Primary Examiner*—Courtney Thomas
(74) *Attorney, Agent, or Firm*—Kiran Malhotra (57) ABSTRACT

A system and method for automatic digital radiographic inspection of piping in which a radiation source and radiation detector are mounted on an inner carriage that rotates concentrically inside an outer carriage and both carriages are placed externally to the piping during operation. A rotating system is provided to cause the inner carriage to rotate completely around the piping. A positioning system is provided for moving the outer carriage longitudinally on the piping. A balancing system is provided such that any tilting of the system during its longitudinal movement on the piping is corrected. In operation, the system is placed on the piping and the rotating system causes the inner carriage to rotate around the piping. After one complete rotation is ensured the positioning system moves the assembly in a longitudinal direction on the piping. A controller controls the rotating; positioning and balancing systems in a coordinated manner to move the outer carriage after the inner carriage has made one complete rotation of the piping. The radiation detector receives the data signals form the radiation source and these signals are used to generate images of the piping for inspection of defects.

7 Claims, 6 Drawing Sheets

METHOD AND APPARATUS FOR AUTOMATED, DIGITAL, RADIOGRAPHIC INSPECTION OF PIPING

FEDERAL SPONSORED RESEARCH

Not Applicable

SEQUENCE LISTING OR PROGRAM

Not Applicable

FIELD OF INVENTION

This invention relates to automatic radiographic inspection and automated image acquisition of piping and other cylindrical vessels used for fluid transport. Fluids such as crude oil, petroleum products, natural gas and other chemicals are transported in piping that is subject to damage in the structure caused by physical, chemical, and electrolytic actions. These actions can weaken the structural integrity of the piping or vessel and can result in oil and chemical spills that cause environmental damage and also can result in fires and explosions. To ensure that the vessel or pipe can continue to be used safely ongoing nondestructive testing is required.

BACKGROUND OF THE INVENTION

The greatest utility of the invention described in this specification is for inspection of piping, but the invention can be used to inspect other types of hollow containers such as heat exchangers and silo sections used to transport fluids. Piping is vulnerable to attack by internal and external corrosion, cracking, mechanical damage and manufacturing flaws in the manufacturing process as well as needs to remain undamaged during use in the field. Therefore the invention has applicability both before and after installation. Anomalies and flaws can be caused during manufacturing and need to be discovered prior to installation. In addition, physical, chemical and electrolytic actions can cause flaws such as cracks after installation and therefore regular inspection is required to ensure safe operation. Furthermore, in order to minimize energy losses and increase worker safety piping is usually insulated by an external layer of thermal insulation around the outside diameter of the piping. This layer of insulation makes it more difficult to inspect the piping for flaws. Inspection of piping after installation is more problematic because of the difficulties of access and in the case of piping inspection the apparatus needs to be capable of use over long distances in remote locations. Piping has to be inspected completely around the circumference to detect possible flaws in every portion of the pipe. This requirement further complicates the piping inspection process.

Various methods have been described in the prior art to detect flaws in piping. For example ultrasonic inspection systems have been used. Ultrasonic inspection requires that a sound wave be induced into the surface of the pipe. Typically an electronic generator or transducer generates pulses or periodic sound waves. These sound waves can either be directed along the length of the pipe or perpendicular to the pipe wall. These methods are referred to as shear wave and straight beam respectively. The sound waves bounce of the pipe walls and also off anomalies or discontinuities and the echoes are measured by a receiving transducer. The speed of the echoes are measured to develop an accurate description of the internal nature of the pipe walls. Most piping is insulated to minimize energy losses and increase worker safety. Typically the piping is wrapped with layers of insulating foam and surrounded with a protective layer of stainless steel or aluminum. The primary drawback of the ultrasonic systems is that intimate contact of the generator with the pipe surface is required. Because sound waves are reflected by the insulation layer the insulation and protective layers need to be removed from the pipe for accurate inspection by ultrasonic devices.

Radiographic techniques have been used to inspect piping and hollow vessels. X-rays for example being electromagnetic waves are unaffected by the insulation layer. X-rays penetrate the insulation as well as the pipe wall and impinge on X-ray receptive film that captures the images of the vessel or piping. After the film is exposed to the radiation it needs to be developed. One needs chemicals to develop the image on the film and these chemicals need to be safely disposed. The entire process can take ten to fifteen minutes per film image. When imaging a pipe of six or more inches in diameter, three or more images are necessary to ensure complete coverage of the pipe. Pipes greater than 12 inches in diameter require additional images needing more time and more chemicals to dispose.

Internal pipe crawling devices equipped with X-ray equipment have been described in the prior art. The external X-ray source and the internal X-ray detector need to be aligned for the X-ray detector to receive the data signals. One has to ensure that during the movement of the device that it does not climb the internal walls thereby causing rocking motions and disturbing the alignment of the X-ray source and the detector. If the X-ray source and the detector are not aligned then the accuracy and quality of the resulting images are adversely affected. It may also be necessary to stop fluid flow in the piping during the inspection process.

BRIEF SUMMARY OF THE INVENTION

The invention described below provides a system and a method for high speed radiographic inspection of piping that can be used in remote locations on insulated pipe of varying diameters, providing highly accurate images on all portions of the piping by its ability to rotate circumferentially around the piping. The radiation source and detector are supported on an inner carriage in such a way that they are perfectly aligned with each other. The inner carriage is capable of 360 degree rotations around the pipe and is supported by an outer carriage that rests on the piping. The inner and outer carriages are concentric with each other and are both located outside the piping. The inner and outer carriages are open on one end to enable placement of the system at any location on the piping. The inner carriage is designed such that it is always supported by the outer carriage during the 360 degree rotation around the piping. In operation means are provide to rotate the inner carriage in either the clock wise or the counter clockwise direction. Sensing devices are provided to stop the rotation when a complete 360 degree rotary traverse has been made. Positioning means are provided to move the device longitudinally to the next location. At the next location the inner carriage can be rotated in the opposite direction by way of example and not as a limitation to save time of inspection. Balancing means are provided to ensure that the device stays in alignment on the piping. The rotary and longitudinal movements are coordinated by a control console. The system uses self contained low voltage radiation source and sensitive digital radiation detector that can detect the signals from the source. The inner cage rotates around the pipe and the radiation is continuously detected and creating single line images of the pipe. Once the inner cage has rotated 360 degrees the computer software converts all the image lines into a complete image of the pipe section that can be inspected in real time by the operator or archived for later inspection. The rotation and moving steps are repeated until the desired length of piping has been inspected.

The present invention and its advantages over the prior art to inspect piping will become apparent upon reading the following detailed description and the appended claims with reference to the drawings that are part of the specification of the invention.

DRAWINGS

Reference Numerals 10 system for the radiographic inspection of piping
20 outer carriage
30 inner carriage
40 control box
90 piping
100 control console
101 power and interface cable
102 x-ray source
103 radiation detector
104a, 104b, 104c, 104d critical support rollers
105 supporting rollers
106 motor for inner carriage rotation
107a, 107b motors for longitudinal movement
108 housing for balancing pendulum and rotational sensor
111 inner carriage drive chain
112a, 112b front wheel rollers
112c, 112d rear wheel rollers
113a, 113b driving sprockets
114 sprocket drive chain
115a, 115b motor drivers
116 balancing pendulum
117 rotational sensor
118 home position plate
119 variable resistor

DETAILED DESCRIPTION OF THE INVENTION

Figure 1:
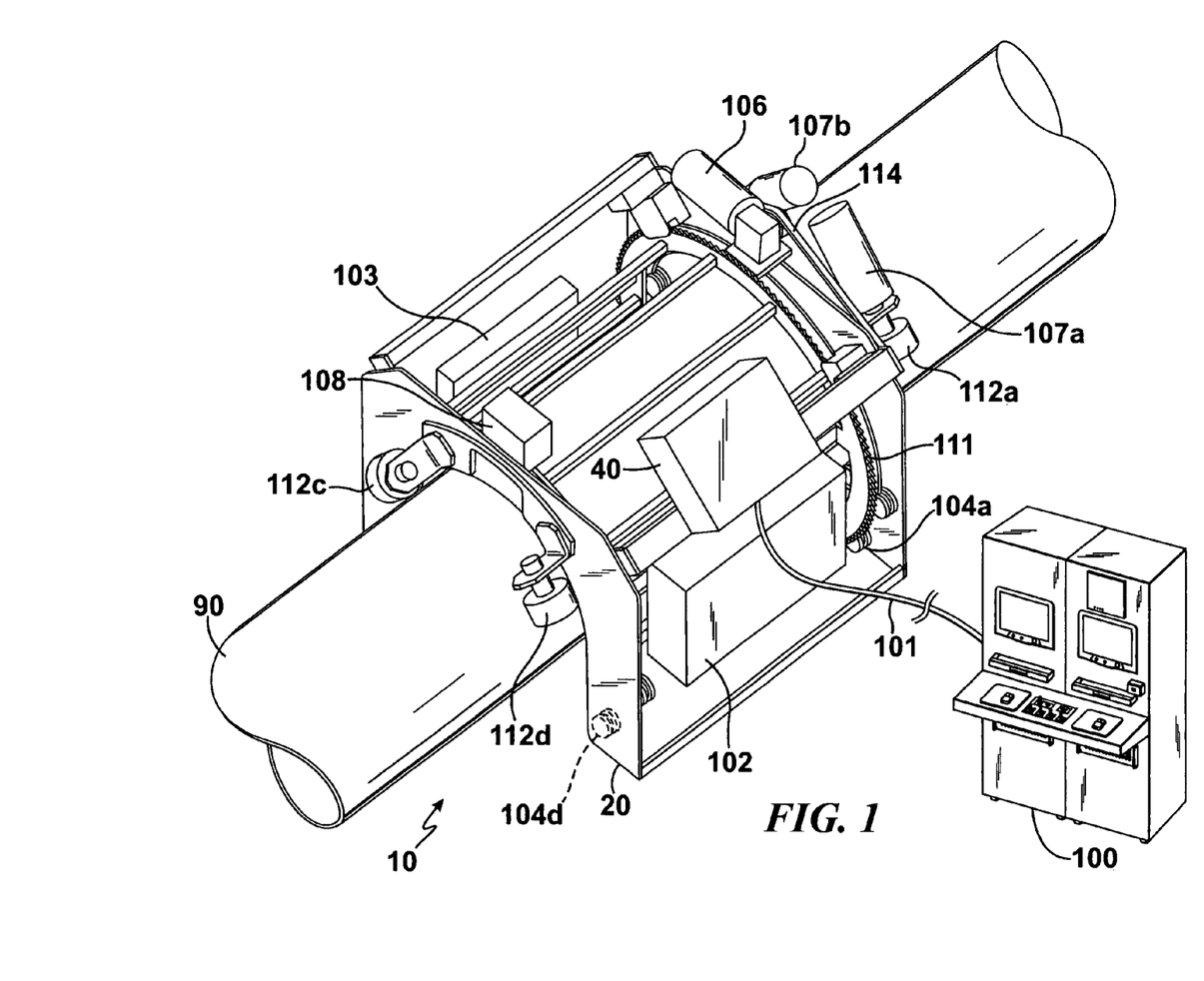
FIG. 1 shows a perspective view of the radiographic inspection system for the inspection of piping and other fluid transport vessels.

Referring to the drawings wherein identical reference numerals denote the same elements throughout the various views. FIG. 1 shows the system for x-ray inspection of piping. As mentioned before this system is not restricted to piping and could also be used for inspecting other cylindrical fluid transport vessels such as heat exchangers and silo sections. The system can be used to inspect piping prior to installation although its greatest utility is to measure insulated piping after installation.

Figure 2:
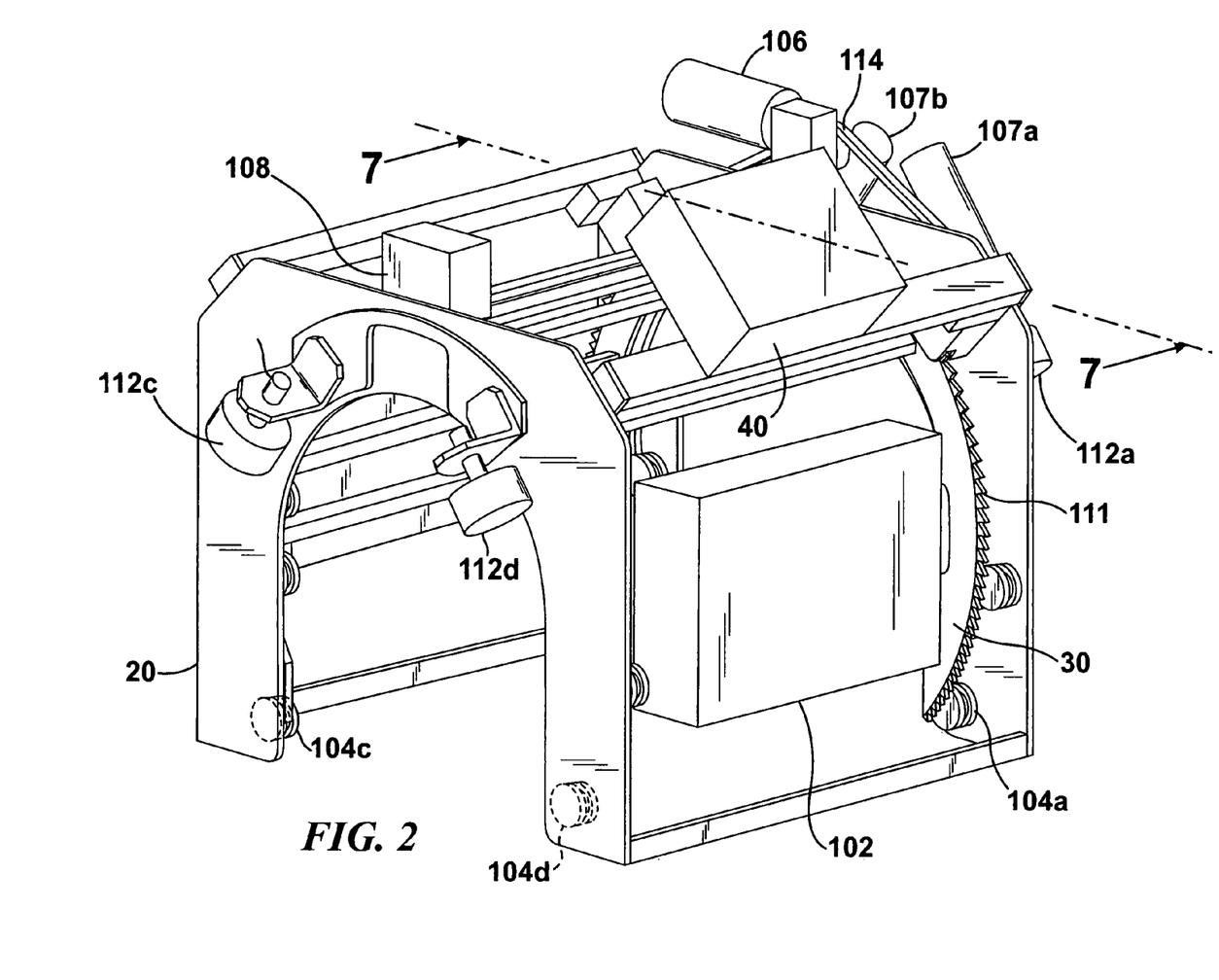
FIG. 2 shows a perspective view of the inner carriage supported by the outside carriage and the x-ray source from one end of the system.
Figure 3:
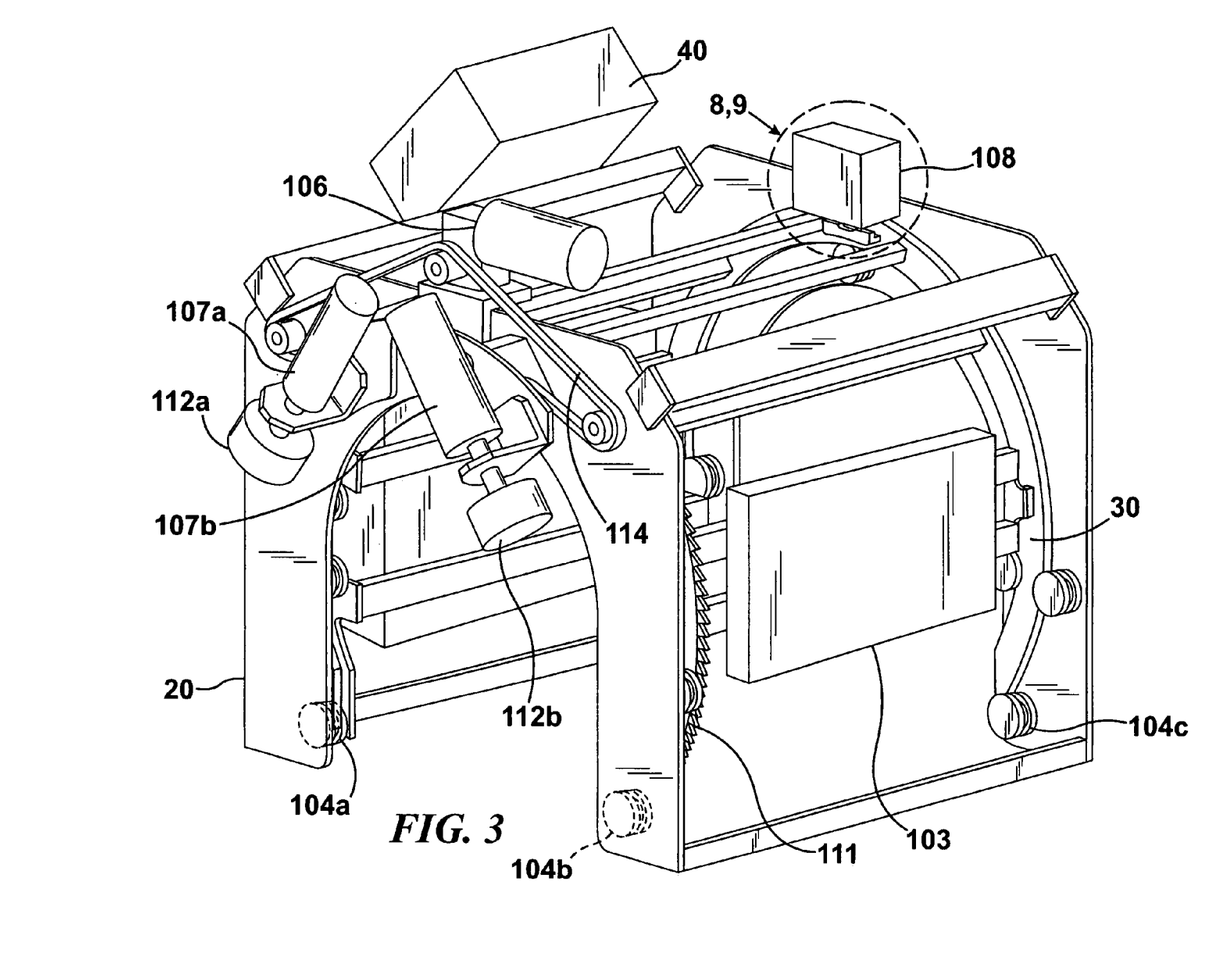
FIG. 3 shows a perspective view of the inner carriage supported by the outer carriage and the radiation detector as seen from the other end of the system.
Figure 4:
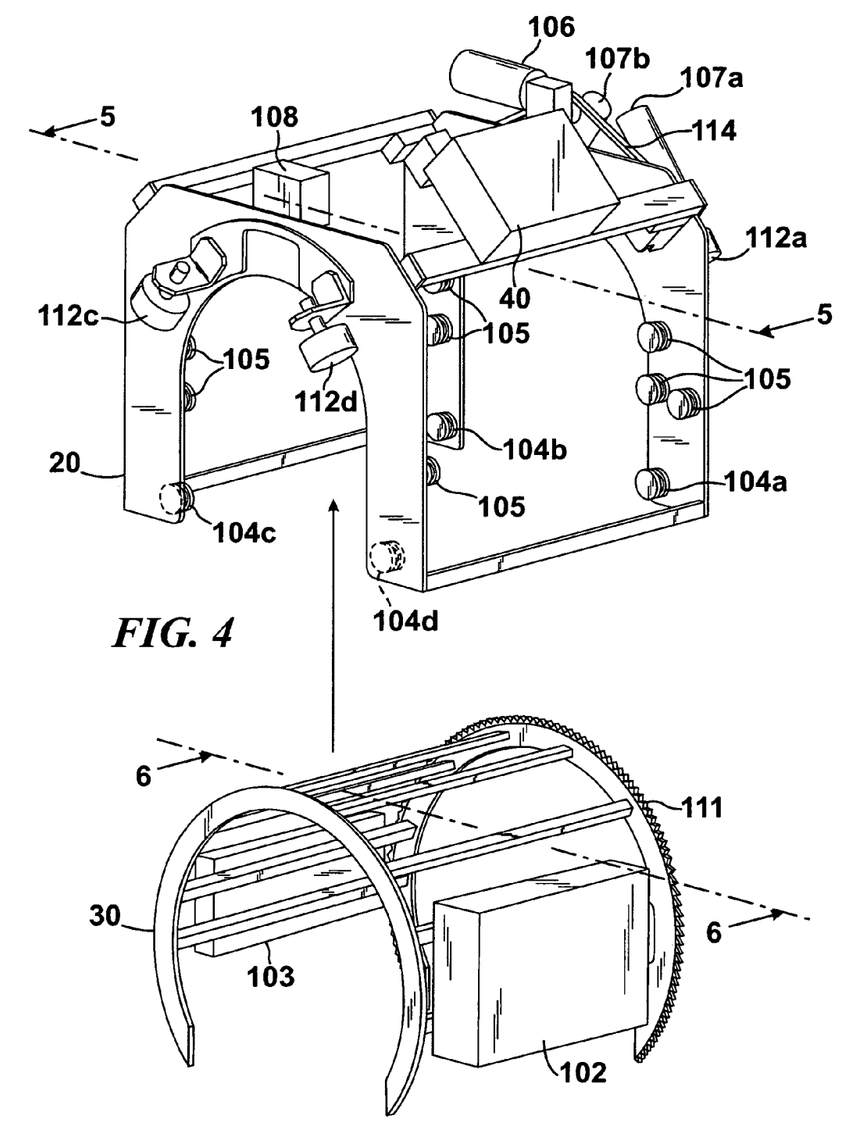
FIG. 4 shows separate perspective views of the outer carriage and the inner carriage.
Figure 5:
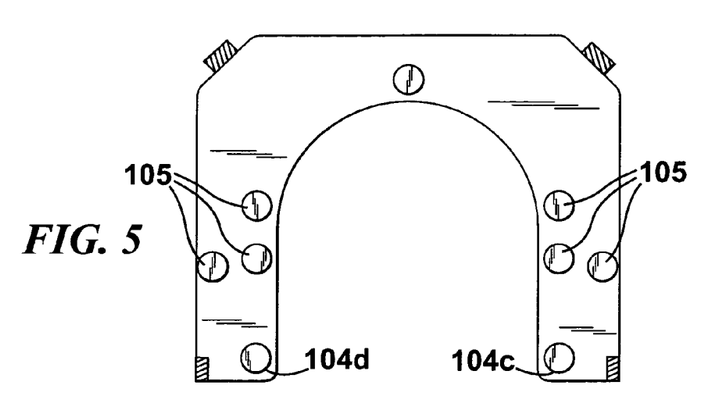
FIG. 5 shows a sectional view of the outer carriage taken through section line 5-5 in FIG. 4.
Figure 6:
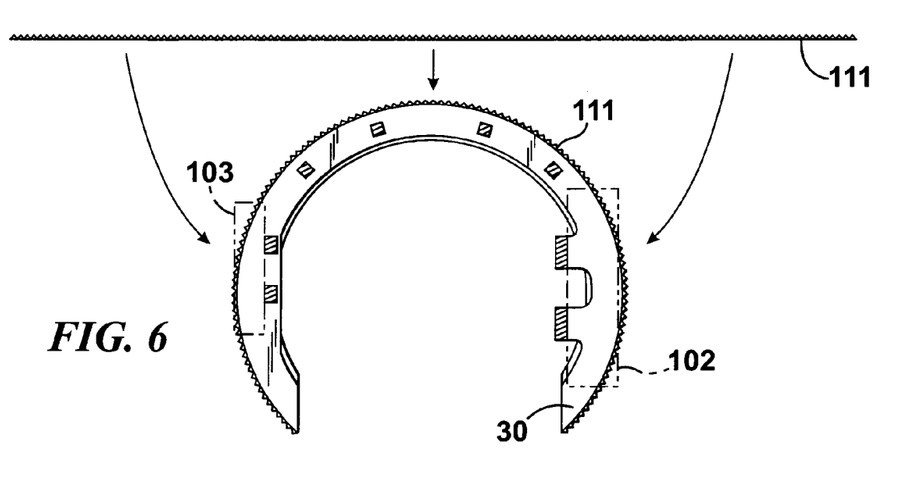
FIG. 6 shows a sectional view of the inner carriage and drive chain taken through section line 6-6 in FIG. 4.

FIG. 1 shows the system mounted on the piping. FIGS. 2, 3 and 4 show the openings in the bottom portions of the inner carriage 30 and outer carriage 20 that allows the system to be placed on the piping. As best shown in FIG. 4 the outer carriage is provided with four critical support rollers 104a, 104b, 104c and 104d. Two rollers are attached to one end frame of the outer carriage and two are attached to the opposite end frame of the outer carriage. The distance between the two sets of support rollers is somewhat larger than the diameter of the piping including the insulation. For example, but not as a limitation, a 12 inch diameter pipe line when insulated has an outside diameter of app. 20 inches. The distance between the centers of the support rollers would measure approximately 23 inches. The inner carriage opening would be approximately 21 inches thereby allowing placement of the system on the pipeline at any point along the length of the pipe line. In addition to the four critical support rollers, a plurality of support rollers 105 are provided to support the inner carriage. Typically, but not as a limitation, 12 support rollers, 6 on each side may be provided to support the inner carriage in addition to the four critical support rollers.

As shown in FIGS. 2 and 3 the x-ray source 102 and the radiation detector 103 are mounted on the inner carriage 30 such that are perfectly aligned with each other. A balancing weight (not shown) is mounted on the side of the inner carriage where the radiation detector is mounted to equal the weight of the x-ray source. The x-ray source 102 used in the referred embodiment is a self contained solid state x-ray source that permits the use of a low voltage linear diode array detector 103 and the combination of this type of x-ray source and detector is light weight and modular thereby enhancing the portability of the system. However, it is possible to use other types of x-ray sources and detectors that are available in the market including isotopic gamma ray producing radiation sources and other types of detectors that are well known in the art.

Figure 7:
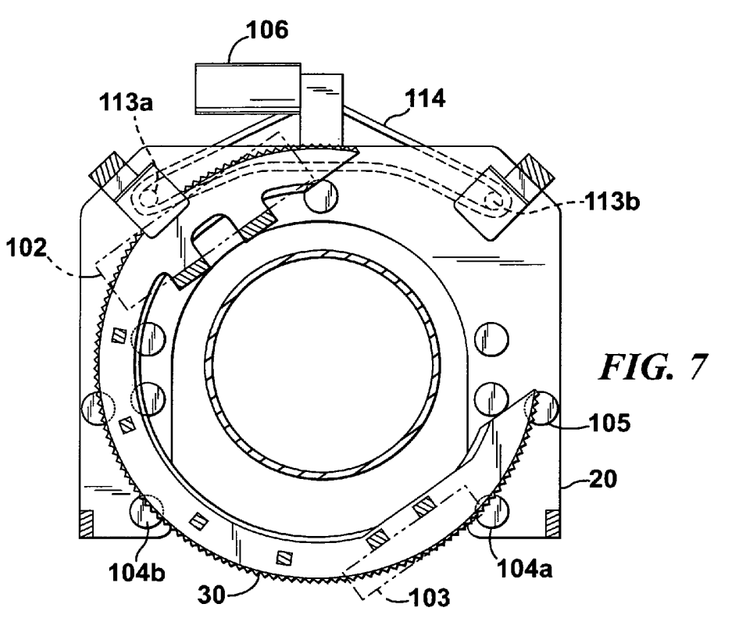
FIG. 7 shows a sectional view of the system taken through section line 7-7 in FIG. 2.

As is best seen in FIG. 3 a motor 106 is mounted on the outer carriage to drive the inner carriage and cause it to rotate in either the clockwise or the counterclockwise direction. In the preferred embodiment as shown in FIG. 7 the motor 106 is connected to the inner carriage drive chain 111 via sprocket drive chain 114 and drive sprockets 113a and 113b. The motor 106 is provided with an encoding device that is standard in the art and that signals the control console 100 as to the exact location of the inner carriage in relationship to the circumference of the piping. Alternative driving mechanisms to rotate the inner carriage based on gear and tooth system or a belt and pulley system or a cam drive system can be designed by one skilled in the art.

As is best seen in FIG. 1 the outer carriage is supported on the piping by four wheel rollers 112a, 112b, 112c and 112d. In the preferred embodiment the front wheel rollers 112a and 112b are driven by motors 107a and 107b to move the system longitudinally on top of the piping. The motors are provided with encoding devices well known in the art that provide the control console 100 with the exact location of the system from a reference point on the piping. Other variations would include driving the rear wheel rollers 112c and 112d or driving all four wheel rollers.

Figure 9:
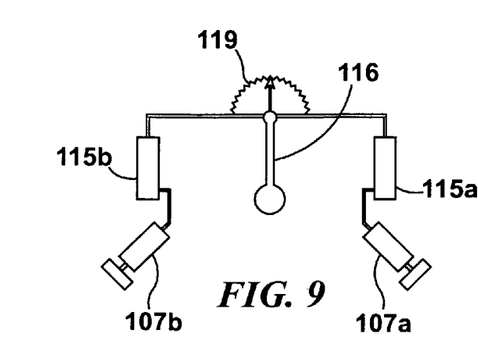
FIG. 9 shows the balancing pendulum

The housing 108 shown in FIG. 1 contains a balancing pendulum 116 and the rotational sensor 117. FIG. 9 shows the working mechanism of the balancing pendulum. In the preferred embodiment the balancing pendulum is used to sense any tilt in the system as it moves longitudinally on the piping. This tilting causes the variable resistor 119 to send an electrical signal to the motors 107a and 107b via motor drivers 115a and 115b to increase the speed of one motor with respect to the other such that the tilt is corrected. Other balancing mechanisms such as gyroscopes can be used to accomplish the same purpose.

Figure 8:
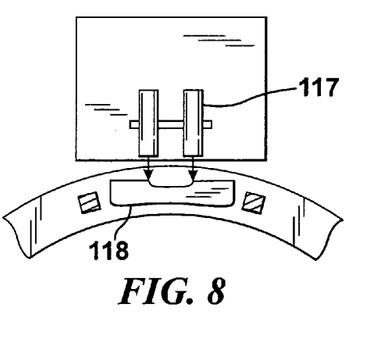
FIG. 8 shows the rotational sensor.

As shown in FIG. 8 the rotational sensor 117 consists of two capacitive switches, one detecting the start of the rotation and the other the completion of one complete rotation around the circumference of the piping. At the start of the rotation the leading switch senses one edge of the home position plate 118. The rotation is stopped only after the trailing switch reaches the same edge of the home position plate thereby ensuring that a complete 360 degree rotation plus an overlap of approximately 15 degrees is achieved. Other types of devices such as optical sensors and mechanical switches can be used to achieve the same purpose. The rotary sensor works in conjunction with the encoder on the drive motor 106 for inner carriage rotation to identify the exact location of the pipe portion that is being inspected.

The control console 100 is located remotely from the system 10. The control console contains computers capable of interpreting the x-ray images generated by the x-ray source 102 and the radiation detector 103. Software programs (not claimed in this invention) coordinate the rotation of the inner carriage, the longitudinal movement of the system along the piping, the balancing and the rotary systems. The control console is connected to the control box 40 shown in FIG. 1. The control box is connected to the various components of the system 10. In the preferred embodiment the signals between the control console and the control box are sent through the power and interface cable 101. Alternatively these signals can be sent by wireless means that are available in the art.

Operation

In order to produce a x-ray scan of the pipe or vessel the assembled system 10 would first be placed onto the piping 90. When the inner carriage 30 and outer carriage 20 are rotated to home positions the bottom of the system is open providing a clearance gap. The distance between the rollers 104a and 104b and 104c and 104d is greater than the overall diameter of the piping and the bottom opening in the inner carriage is also greater than the overall diameter of the piping creating a clearance gap permitting the system to be placed on top of the piping.

When an image of a pipe section is desired the system is activated and signals are sent to the control box 40 instructing the system to begin acquiring an image. The x-ray source 102 is then activated and the radiation from the x-ray source travels through the pipe or vessel and strikes the radiation detector 103 on the opposite side of the pipe. The radiation detector is capable of creating a single line of pixels that digitally represents the cross section thicknesses of the pipe and this digital signal is sent to the control console 100 where the computer generates this into a single line of an image. The motor 106 then begins to rotate the inner carriage 30 within the outer carriage 20. As the inner carriage rotates the x-ray source and the radiation continue to work together to create additional image lines.

FIG. 7 shows one position in the rotation of the inner carriage around the piping. The inner carriage remains supported at every point in the rotation by the critical supporting rollers 104a, 104b, 104c, 104d and the supporting rollers 105. The rotational sensor 117 sends a signal to the control console 100 when the rotation around the circumference of the piping is completed. On completion of the rotation the x-ray source 102 and the radiation detector 103 have been rotated by 360 degrees plus an overlap of about 15 degrees that is controlled by the switch mechanism of the rotational sensor as described above thereby ensuring that a complete image of the targeted section of the pipe is created.

Once a single section of pipe has been completely scanned the system can be moved to another section or the next incremental section of the pipe or vessel. A signal from the control console 100 is sent to the control box 40 and the motors 107a and 107b are activated causing the front wheel rollers 107a and 107b to rotate. The rear wheel rollers 107c and 107d support the rear end of the outer carriage 20 as shown in FIG. 1 and rotate freely as the outer carriage moves longitudinally along the piping to the next location. Any tilting of the outer carriage during the longitudinal movement is corrected by the balancing pendulum 116 as described above.

The system 10 is then ready to begin another rotation of the new section of the vessel or pipe. In the preferred embodiment the next rotation is in the opposite clock direction as to the previous rotation. This mode saves time as the system 10 moves in a longitudinal direction on the piping.

What is claimed is:

1. A system for radiographic inspection of piping comprising:
   a) an inner carriage rotatably mounted on an outer carriage such that the inner carriage is concentric with the outer carriage and with the piping on which the outer carriage rests;
   b) an x-ray source and a radiation detector mounted on the inner carriage, the x-ray source and the radiation detector being positioned on opposite sides of the piping;
   c) rotating means for moving the inner carriage circumferentially around the piping in clockwise and counter clockwise directions;
   d) positioning means for moving the outer carriage longitudinally in relationship to the piping;
   e) balancing means for aligning the outer carriage during longitudinal movement on the piping;
   f) sensing means for tracking the position of the inner carriage and ensuring one complete circumferential revolution of the inner carriage around the piping;
   g) a controller for controlling the rotating means, the positioning means, the balancing means and the sensing means in a coordinated manner so that the outer carriage is moved only after the inner carriage has made one complete circumferential rotation, the outer carriage remains in alignment during longitudinal movement and the locations of the images around the circumference of the piping received by the radiation detector are identifiable;
   h) an imaging unit that receives data signals from the radiation detector and archives the images.

2. The system of claim 1 wherein the rotating means is a chain mounted on the inner carriage that is driven by sprockets connected by a drive chain to a drive motor.

3. The system of claim 1 wherein the positioning means comprises a set of two motors that drive two of the four supporting wheels that are attached to the outer carriage and rest on the piping.

4. The system of claim 1 wherein the balancing means is a pendulum that senses when the outer carriage is not in alignment with the piping and sends an electrical signal to adjust the relative speeds of the two motors thereby re-aligning the outer carriage on the piping.

5. The system of claim 1 wherein the sensing means is a capacitor sensor with leading and trailing switches in combination with an encoder that monitors the position of the inner carriage in relation to the piping.

6. A method for radiographic inspection of piping, which comprises:
   a) providing an inner carriage rotatably mounted on an outer carriage and placing the outer carriage on the piping such that the inner carriage is concentric with the piping;
   b) providing an x-ray source and radiation detector mounted on the inner carriage such that the x-ray source and radiation detector are aligned on opposite sides of the piping;
   c) causing the inner carriage to rotate circumferentially around the piping in either the clockwise or counter clockwise directions;
   d) sensing one complete circumferential rotation around the piping;
   e) moving the outer carriage longitudinally after completion of the circumferential rotation of the inner carriage;
   f) repeating the steps of rotation and longitudinal motion successively until the desired length of the piping has been inspected;
   g) sensing the circumferential location of image data signals received by the radiation detector;
   h) balancing the outer carriage as it is moved longitudinally in relationship to the piping.

7. The method of claim 6 further comprising collecting the image data signals received by the radiation detector and archiving the image data signals for inspection of defect in the piping.

* * * * *